United States Patent [19]

Schramm

[11] Patent Number: 5,281,539
[45] Date of Patent: Jan. 25, 1994

[54] IMMUNOASSAY DEVICE FOR CONTINUOUS MONITORING

[75] Inventor: Willfried Schramm, Ann Arbor, Mich.

[73] Assignee: The Regents of The University of Michigan, Ann Arbor, Mich.

[21] Appl. No.: 676,767

[22] Filed: Mar. 27, 1991

Related U.S. Application Data

[63] Continuation-in-part of Ser. No. 416,160, Oct. 2, 1989, abandoned.

[51] Int. Cl.$^5$ ............... G01N 27/08; G01N 27/327; G01N 23/553
[52] U.S. Cl. .................... 436/518; 204/400; 204/403; 204/409; 204/415; 422/57; 422/58; 422/82.01; 422/82.02; 435/7.9; 435/7.93; 435/288; 435/291; 435/817; 436/524; 436/525; 436/806; 436/807
[58] Field of Search ............... 422/56–58, 422/82.01, 82.02; 435/7.9, 288, 291, 817, 7.93; 436/518, 524, 525, 528, 544, 806, 807; 204/400, 403, 409, 415

[56] References Cited

U.S. PATENT DOCUMENTS

| | | | |
|---|---|---|---|
| 4,228,237 | 10/1980 | Hevey et al. | 435/7.5 |
| 4,277,560 | 7/1981 | Gray et al. | 435/291 |
| 4,803,170 | 2/1989 | Stanton et al. | 436/518 |
| 4,868,108 | 9/1992 | Bahar et al. | 435/4 |
| 5,124,253 | 6/1992 | Foulds et al. | 435/817 |

*Primary Examiner*—David Saunders
*Assistant Examiner*—Christopher L. Chin

[57] ABSTRACT

A device and process for detecting the presence of organic molecular analytes in a fluid comprising a first binding component having a predetermined first affinity for specifically reversibly binding an analyte, a molecular conjugate of the analyte with a signal generating molecule that generates a detectable signal, and a second binding component having a predetermined second affinity for reversibly binding the signal generating molecule. In the presence of analyte, a fluid conducting system allows competitive binding of the analyte with the molecular conjugate and causes displacement of the conjugate and conducts the displaced conjugate to the second binding component. The signal generating molecule generates a detectable signal distinguishing binding thereof at the first or second binding components thereby indicating the presence of the analyte in the fluid.

2 Claims, 5 Drawing Sheets

IMMUNOASSAY DEVICE FOR CONTINUOUS MONITORING

This application is a continuation-in-part of U.S. Ser. No. 07/416,160, filed Oct. 2, 1989, now abandoned.

TECHNICAL FIELD

This invention relates to a device and process for detecting the presence of organic molecular analytes in a fluid. More specifically, the invention relates to a device and process for using either a discontinuous, single use disposable analytical device or a continuous use device for continually measuring concentration changes of substances such as hormones, drugs, or various other biologically active substances in the submicrogram range with a specificity comparable to a radioimmuno assay.

BACKGROUND OF THE INVENTION

Various methods have been derived for monitoring low molecular weight compounds in blood plasma or other biological media. For example, enzyme electrodes have been used for the direct measurement of biomolecules in physiological samples, such as glucose, urea, amino acids, and others. These enzyme electrodes include a selective enzyme layer immobilized at the surface of a potentiometer or amperometeric device that senses the steady state concentration of a product formed in the immobilized layer as the substrate for the enzyme diffuses into this reactive film.

The U.S. Pat. No. 4,344,438 to Schultz, issued Aug. 17, 1982 discloses an optical sensor for monitoring low molecular weight compounds in blood plasma. The device utilizes a binding protein immobilized inside a membrane. A conjugate between glucose and fluorescein serves to generate a signal. The conjugate binds to an immobilized lectin in the absence of glucose such that there is no fluorescence in an adjacent dialysis chamber. If glucose enters into the lumen through the membrane, it competes with binding sites on the lectin and sets free glucose fluorescein conjugate, hence there is fluorescence in the detector tube. It is disadvantageous to use enzymes as signal generators in this system because the dissociated conjugate in the presence of glucose in the middle of the detector tube could provide a high background signal so that the reduced amount of conjugate on the side of the tube might not be distinguishable from the background or from the previous signal where no external glucose was present.

The U.S. Pat. No. 4,517,288 to Giegel et al, issued May 14, 1985 discloses a method for conducting a ligand assay in an inert porous medium wherein a binding material is immobilized within the medium. The method includes the steps of immobilizing a binding material within a finite zone of a medium and applying an analyte to the zone containing the immobilized binding material. A labeled indicator is applied to the zone and becomes bound within the zone in an amount which can be correlated to the amount of the analyte in the zone. A solvent is applied to the center of the zone to chromatographically separate the unbound labeled indicator from the zone and measuring the amount of labeled indicator remaining in the zone. This chromatographic method cannot be used in a continuous assay device for continually determining changes in a dynamic system.

Anderson et al reported in Clin. Chem. 34/7, 1417-1421 (1988) of a fiberoptic chemical sensor for continuous, reversible measurement of phenytoin. Beta-phycoerythrin-phenytoin and Texas Red-labeled antibody to phenytoin were sealed inside a short length of cellulose dialysis tubing. The tubing was cemented to the distal end of an optical fiber. When the sensor was alternately placed into solutions with various concentrations of free phenytoin, the drug crossed the dialysis membrane and displaced a fraction of the beta-phycoeythrin-phenytoin from the antibody. The resulting change in fluorescent signal was measured with a fiberoptic fluorometer. A reversible sensor could be made that has a response time suitable for continuous measurements utilizing the invention. In an abstract presented at the proceedings of the symposium on Sensor Science and Technology, Apr. 6-8, 1987 and published in the same proceeding abstracts by the Electrochemical Society, Inc. of Pennington, N.J., Vol. 87-15, W. Schramm, et al (the inventor of the present application) postulated an immunoglobulin-based biosensor including heterobifunctional structures that bind reversibly to immobilized counterparts. A combination of two antibody-antigen reactions hypothetically would generate a signal for continuous monitoring of analytes. The abstract hypothesizes several biosensor systems, the abstract being published prior to any attempt at reduction to practice of the concept.

The present invention provides means for constructing either a discontinuous single use disposable analytical test device or a reversible biosensor for continuous measurements of analytes. The invention utilizes the concept of a dislocated conjugate, such as the general concept being disclosed in the Shultz patent, but goes further so as to bind the conjugate at another site and measure it at that second site. Accordingly, the present invention can utilize enzymes as a signal generator. Further, the present invention can generate two signals, one at each of the two binding sites.

SUMMARY OF THE INVENTION

In accordance with the present invention, there is provided a device for detecting the presence of organic molecular analytes in fluid, the device including first binding means having a predetermined first affinity for specifically, reversibly binding the analyte, and a molecular conjugate of the analyte with a signal generating molecule which generates a detectable signal. Second binding means has a predetermined second affinity for reversibly binding the signal generating molecule. Fluid conducting means conducts the fluid to the first binding means allowing competitive binding of the analyte in the fluid and displacement of the conjugate and for conducting the displaced conjugate to the second binding means. The signal generator molecule generates a detectable signal distinguishing binding thereof at the first or second binding means thereby indicating the presence of analyte in the fluid.

The present invention further provides a process for detecting the presence of organic molecular analytes in the fluid, the method including the steps of binding the molecular conjugate of the analyte coupled to the signal generating molecule, which generates the detectable signal, to a first binding molecule having a predetermined first affinity for specifically reversibly binding the analyte and conducting the fluid to the first binding molecule and competitively binding analyte in the fluid and displacing bound conjugate. The displaced conjugate is conducted to a second binding molecule having a second affinity for reversibly binding the signal generating molecule. A detectable signal is generated which distinguishes binding of the conjugate at the first or second binding molecules thereby indicating the presence of analyte in the fluid.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE DRAWINGS

A device for detecting the presence of organic molecular analytes in a fluid is generally shown as 10 in the Figures. Primed numerals are used to indicate similar structures between the several embodiments.

The term analyte is used herein to mean any molecular species within a body fluid, such as progesterone, testosterone, and benzoylecgonine. Conceivably, the present invention could also be used for the determination of other organic and inorganic species of molecules present in various fluids which are not necessarily body fluids or organic fluids.

Generally, the invention comprises the combination of first binding means having a first affinity for specifically reversibly binding the analyte, a molecular conjugate of the analyte with a signal generating molecule, referred to as a heterobifunctional complex, second binding means having a second affinity for reversibly binding the signal generating molecule, and a fluid conducting mechanism for conducting the fluid to the first binding means allowing competitive binding of the analyte in the fluid and displacement of the conjugate from the first binding means and for conducting the displaced conjugate to the second binding means. The signal generator molecule generates a detectable signal distinguishing binding thereof at the first or second binding means thereby indicating the presence of analyte in the fluid. The invention thereby provides a shuttle signal generating mechanism capable of qualitatively or quantitatively measuring analyte in the fluid.

The ratio of binding affinity of the first binding component and second binding component to their respective counterpart of the molecular conjugate, or the ratio of concentrations of the first binding component and the second binding component are adjusted such that in the absence of analyte, the molecular conjugate is predominately bound to the first binding component. In this state, a signal is generated by means of the molecular conjugate on the first binding component.

Figure 1:
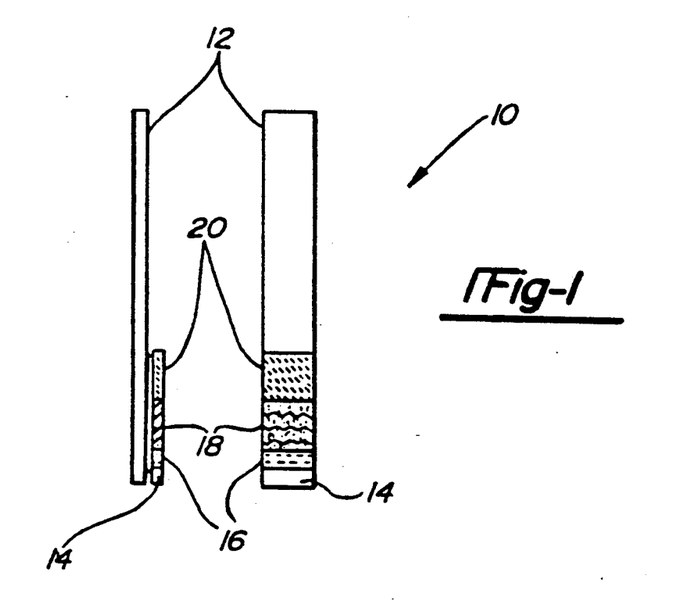
FIG. 1 is a schematic representation of a first embodiment of the present invention shown in plan and side views.

A first embodiment of the invention is generally shown at 10 in FIG. 1. This embodiment of the invention is a disposable test strip for the detection of complex organic molecules in liquids. The presence of the analyte in the liquid sample is indicated on the test strip 10 by a signal, such as a color, at a distinct location on the test strip 10. The absence of the molecule is indicated by a signal at a different distinct location on the test strip 10.

More specifically, the test strip 10 includes a support strip 12. The support strip 12 can be made from a polymer, such as Mylar. Four absorbent membranes 14,16,18,20 are attached to the support polymer 12. The absorbent membranes 14,16,18,20 are attached to the polymer strip 12 so as to be adjacent to each other.

Absorbent membrane 14 provides a conducting means for transporting medium by capillary action to membrane 16. Membrane 16 is capable of conducting the medium by capillary action to membrane 18, and membrane 18 is capable of transporting the medium by capillary action to membrane 20. Accordingly, the membranes 14,16,18,20 function as the fluid conducting means providing separate adjacent zones to each other.

The first binding means is immobilized, chemically or physically, on absorbent membrane 18. This first binding means specifically binds the analyte to be measured. The second binding means is immobilized on membrane 20. The first and second binding means function as bioreceptors for specifically binding either the analyte or signal generator. The first and second binding means can be selected from the group consisting essentially of lectins, receptors, membrane proteins, transport proteins, ribonucleic acid, complimentary subunits, monoclonal and polyclonal antibodies, and other compounds that selectively and competitively bind to the analyte or signal generator, respectively. The first and second binding means can be a proteinaceous or nonproteinaceous nature. The lectins, receptors, and proteins described above are proteinaceous binding means. Examples of nonproteinaceous reversible binders can be chelating ligands, complexing agents, or charged ligands.

The second binding means is immobilized, either physically or chemically bound, to absorbent membrane 20.

The signal generating means can be selected from a group consisting essentially of enzymes, fluorescent molecules, ultraviolet absorbent agents and other compounds capable of conjugation with the analyte without deletion of the capacity to generate the signal. Accordingly, the second binding means can be a bioreceptor that specifically and reversibly binds the signal generating compound. For example, the membrane 20 may have a monoclonal antibody that binds specifically to a signal generator, such as an enzyme.

The absorbent membrane 16 is impregnated with the conjugate such that the conjugate easily migrates with a water front from the end of the strip 10 as the end of strip 10 is immersed in an aqueous medium. If the signal generating means is an enzyme, the conjugate or heterobifunctional reagent comprises an enzyme covalently bound to the analyte. The enzyme in the conjugate converts a substrate into a product such that the product is distinctively different from the substrate. The product can be measured, such as when the enzyme catalytically converts a colorless substrate into a colored product.

Figure 2:
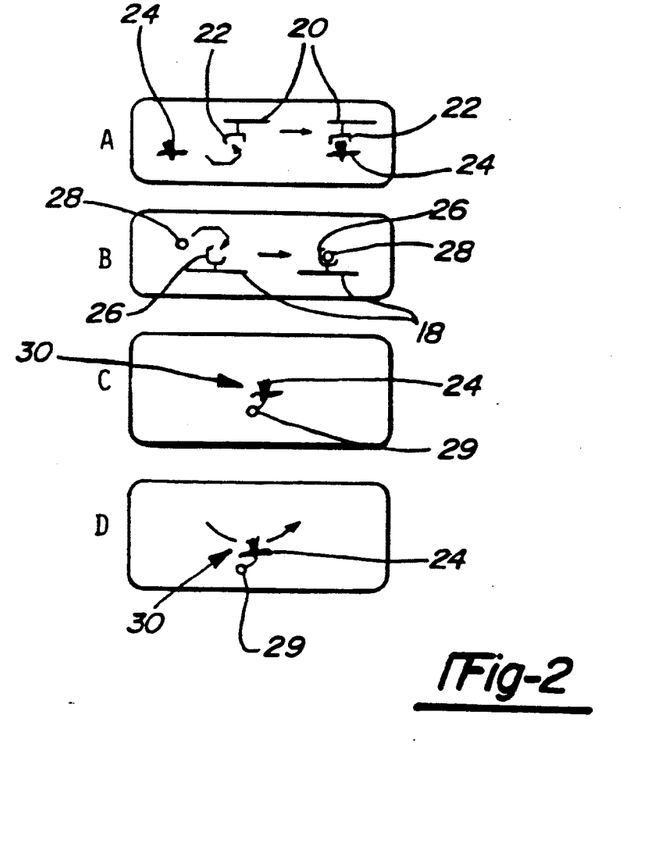
FIG. 2 is a schematic representation of the present invention illustrating the function of each component of the first embodiment of the invention.

The function of each component of the invention is illustrated in FIG. 2. Box A illustrates the second binding means or receptor 22 covalently bound to the membrane 20. The binding molecule 22 is capable of specifically and reversibly binding enzyme 24. Box B in FIG. 2 illustrates the first binding means as specific binding molecule 26 covalently bound to membrane 18, the molecule 26 specifically and reversibly binding analyte 28. Box C schematically illustrates the conjugate 30 of the analyte 29 bound to the enzyme 24. Analyte 29 corresponds structurally and functionally to unbound analyte 28. Box D illustrates the conversion of substrate (S) to product (P) by the enzyme component 24 of the conjugate 30.

Figure 3:
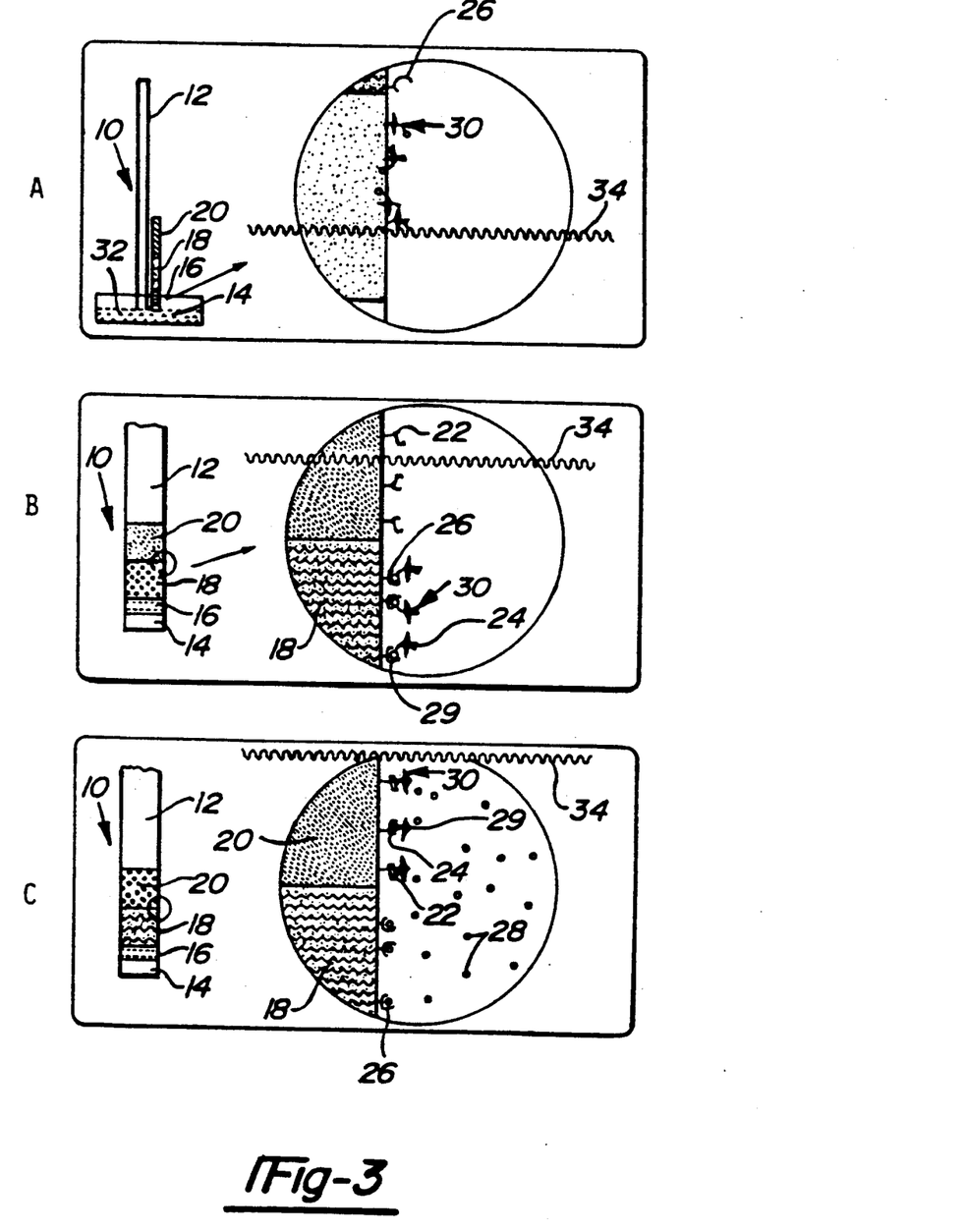
FIG. 3 is a schematic representation of the operation of the first embodiment of the present invention.

The operation of the invention is schematically shown in FIG. 3. The test strip 10 is dipped into a specimen solution 32 as schematically shown in FIG. 3A. The specimen solution is absorbed into the first membrane 14 and carried sequentially through membranes 16,18,20, the solvent front being indicated in the Figures at 34. Each FIG. 3A through C shows the test strip 10 and an enlarged portion of the strip illustrating the detection process.

If no external analyte is present in the specimen solution 32, the conjugate 30 binds to the immobilized binding molecule on the absorbent membrane 18, developing a color on this membrane. This indicates the absence of analyte in the specimen solution 32. Such binding is shown in FIG. 3B. The conjugate 30 will preferentially bind to the binding molecule 26 immobilized on membrane 18 because of the affinity of the binding molecule 26 for the analyte portion 29 of the conjugate 30. Since there is no other competitive binding for the binding molecule 26, the conjugate 30 will bind thereto.

In the presence of free analyte 28 in the specimen solution, the free analyte 28 competes for binding sites with the bound analyte 29 of the conjugate 30 on the binding molecule 26 immobilized at membrane 18. The conjugate 30 diffuses to membrane 20 where it binds to the antibody specifically recognizing the signal generating enzyme 24. Upon exposure to substrate solution, the enzyme 24 develops color on membrane 20 which indicates the presence of free analyte 28 in the specimen solution. In other words, the conjugate 30 either remains on membrane 18, where it is bound, thereby indicating the absence of free analyte, or free analyte competitively binds with the conjugate 30 for binding sites at membrane 18. In this case, the conjugate 30 will not bind totally at membrane 18 and be carried to membrane 20. The conjugate 30 will then bind at membrane 20. Upon being bound at membrane 20, the conjugate 30 is capable of converting substrate to a colored product at membrane 20 thereby indicating the presence of free analyte 28 in the solution.

Figure 4:
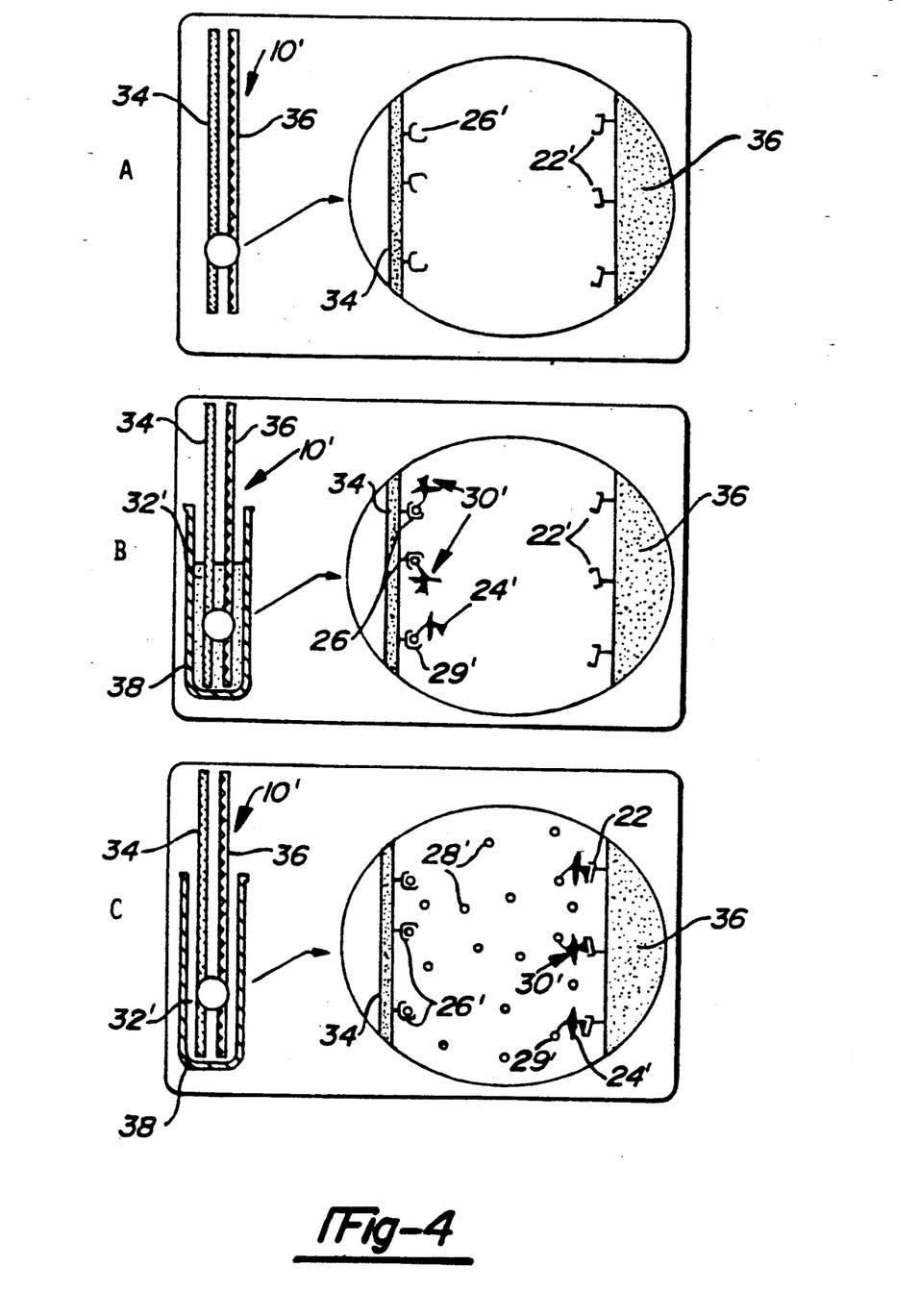
FIG. 4 is a schematic representation of a second embodiment of the present invention and its operation, showing enlarged views.

A second embodiment of the invention is schematically shown in FIG. 4. Rod 34 contains the binding means 26' covalently bound thereto. Rod 36 includes receptor 22' covalently bound thereto. Each of the rods 34,36 can be made from polymers, plastic sheets, glass slides, ceramic, silicon chips, and the like. Each of FIGS. 4A through C illustrate the subject process utilizing the rods 34,36 and further show an enlargement illustrating the invention at the molecular level.

The rods 34,36 are immersed in a tube 38 containing a liquid sample specimen 32' and the heterobifunctional binder 30'. The rods 34,36 are constructed such that the heterobifunctional binder 30' binds predominately only to the binding means 26' (first binding means) recognizing specifically the bound analyte 29' if no external free analyte 28' is present in the sample specimen 32'.

If the rods 34,36 are removed from the specimen sample 32' and exposed to a solution containing substrate (the reaction being illustrated in FIG. 2D), a distinctively measurable product will be detectable and developed on the left rod 34, because the conjugate 30' will bind preferentially to the left rod 34 as opposed to the right rod 36. This is because, as explained above, the totality of bioreceptor 26' on the rod 34 has a greater binding affinity for the analyte portion 29' of the conjugate 30' then the binding means 22' has for the enzyme portion 24' of the conjugate 30'. As discussed above, this may be because of a greater binding affinity per binding means molecule or because of a greater amount of binding means 26' on rod 34 as opposed to binding means 22' on rod 36. Color development on rod 34 thereby indicates that the sample does not contain analyte 28'.

If the sample 32' contains free analyte 28', the free analyte molecules 28' compete for binding sites on the immobilized binding means 26' for the bound analyte 29' on the heterobifunctional binder 30'. The heterobifunctional binder 30' diffuses to the opposite rod 36 and is there eventually bound to the binding means 22' specifically recognizing the signal generating enzyme portion 24' of the heterobifunctional binder 30'.

If the two rods 34,36 are now exposed to a solution containing substrate, only the rod 36 containing the binding means 22' to the signal generator portion 24' of the conjugate 30' develops a distinctively measurable product, such as a color. This indicates that the sample does contain the free analyte 28'.

EXAMPLE

This combination of two antibodies as binders and a heterobifunctional conjugate between a steroid and an enzyme as signal generator has been used for the quantitative determination of progesterone by colorimetric detection. A monoclonal antibody to progesterone was immobilized to the surface of a polyacrylamide rod. Another monoclonal antibody, specifically recognizing horseradish peroxidase (HRP), was immobilized to a polystyrene test tube. The conjugate consists of progesterone-horseradish peroxidase.

Immobilization of antibodies. Monoclonal antibodies of the subtype IgG2bk were purified by ammonium sulphate precipitation and subsequent affinity chromatography on Protein-A immobilized to cyanogen bromide activated agarose. The immunoglobulin was eluted from the Protein-A column by dissociation with acetic acid, pH 3.5, and dialyzed against phosphate buffer, 0.01 mol/L, pH 7.4. The concentration of the antibody was adjusted to 1 mg/mL by UV-spectroscopy at 280 nm absorbance.

The polymer surfaces (polystyrene and polyacrylamide) were coated for 1 h at room temperature with avidin, 1 μg/mL in phosphate buffer in the presence of 1 g/L of glutaraldehyde. The surfaces were washed with de-ionized water containing 1 g/L triton X and subsequently incubated with a solution of 10 and 100 μg/mL of antibody (anti-progesterone and anti-HRP antibody, respectively) in phosphate buffer. The remaining aldehyde functions on the cross-linked avidin were sufficient to bind the immunoglobulins covalently. The surfaces with immobilized antibodies were washed with phosphate buffer containing 1 g/L Trition X and 1 mmol/L sodium cyanoborohydrate. The monoclonal antibody to horseradish peroxidase was immobilized to the polystyrene tube (6 mm ID; Skatron Inc., Sterling, Va.), the monoclonal antibody to progesterone was immobilized to the polyacrylamide rod (4.4 mm OD).

Progesterone-horseradish peroxidase conjugate. Progesterone 11a-hemisuccinate (14 μmol) was dissolved in 0.5 ml of dimethylformamide and 15 μmol of 1-ethyl-3-(3-dimethylaminopropyl) carbodiimide hydrochloride in 200 μL of dioxane was added and stirred for 20 min at room temperature. The reaction mixture was added to a solution of 30 μmol of spermidine (free base) in 300 μL of dioxane and incubated overnight at room temperature. After adding 3 mL of chloroform, the steroid derivative was separated from by-products by extraction with water and recovered from the chloroform phase. The preparation which was recovered by evaporation of chloroform with nitrogen was used for the reaction with horseradish peroxidase (HRP).

HRP (100 nmol) was dissolved in 400 μL of de-ionized water and 200 μL of a solution of sodium periodate in water (0.1 mol/L was added and the solution stirred for 20 min at room temperature.

progesterone derivative was dissolved in 600 μL of dimethyl formamide and slowly added under agitation to the oxidized HRP. The acidity of the solution was raised with sodium carbonate buffer, 0.5 mol/L, to pH 9.5 and 20 μL of sodium cyanoborohydride, 1 mol/L, was added. The reaction mixture was stirred for 2 hours at room temperature and dialyzed against six changes of a total of 4 L phosphate buffer, 0.01 mol/L. The dialyzed solution was purified over a cross-linked polyacrylamide gel exclusion column, P-30 (BioRad, Richmond, Calif.) with a gel volume of 10 mL.

The prepurified HRP-progesterone derivative was finally purified by affinity chromatography. A monoclonal antibody with low affinity to the steroid ($K_a = 7 \times 10^8$ L/mol) was immobilized on cyanobromide activated agarose (5% cross-linked). HRP-progesterone conjugate applied to this gel was eluted with phosphate buffer. Nonreacted enzyme eluted first and was separated from ligand-enzyme conjugate.

Quantitative determination of progesterone. Into each test tube containing a rod, $5 \times 10^{-14}$ mol/L of HRP-progesterone conjugate in 145 μL was added. Thereafter, increasing amounts of progesterone from $1.25 \times 10^{-11}$ g (12.5 pg/tube) to $11 \times 10^{-8}$ g (10 ng/tube) were added in a volume of 5 μL. The solutions were incubated for 90 minutes, the tubes with the rods washed with de-ionized water, separated, and incubated in reagent solution for color development.

HRP was quantitatively determined by oxidation of 3,3',5,5'-tetramethylbenzidine (TMB) and colorimetric detection of the oxidized product at 410 nm. For 100 mL of TMB reagent, 1 mL of a stock solution of 10 mg/mL TMB in dimethyl sulfoxide and 10 μL of a 30% solution of hydrogen peroxide was added citric acid, 0.05 mol/L, pH 4.5. The developing color was stopped after 20 min with sulfuric acid, 1 mol/L, and the absorbance monitored at 600 nm.

Figure 5:
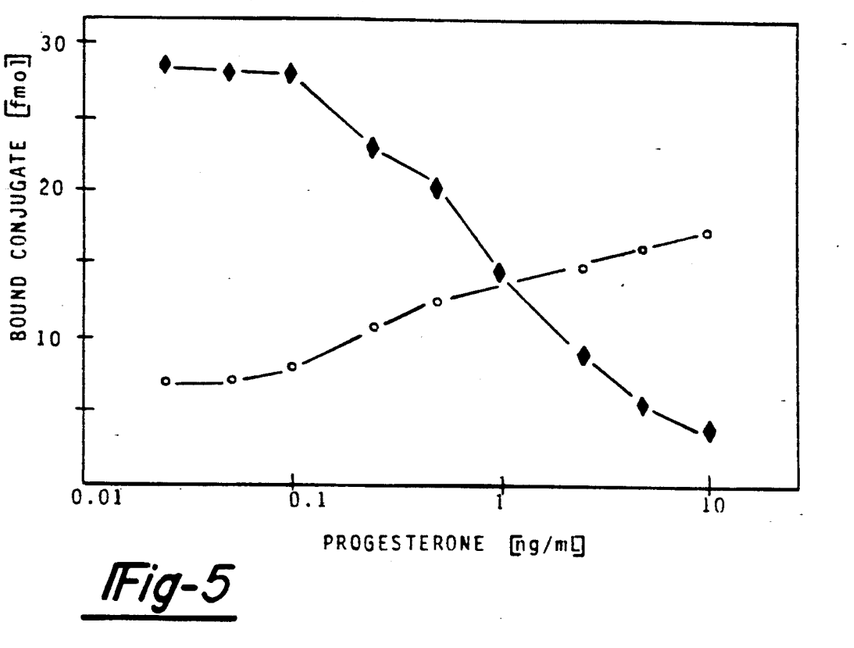
FIG. 5 is a dose response curve of dissociated heterobifunctional conjugate from the immobilized antibody to progesterone (full circles), and associated conjugate on the immobilized antibody to horseradish to peroxidase (open circles) in the presence of increasing amounts of progesterone (x-axis)
Figure 6:
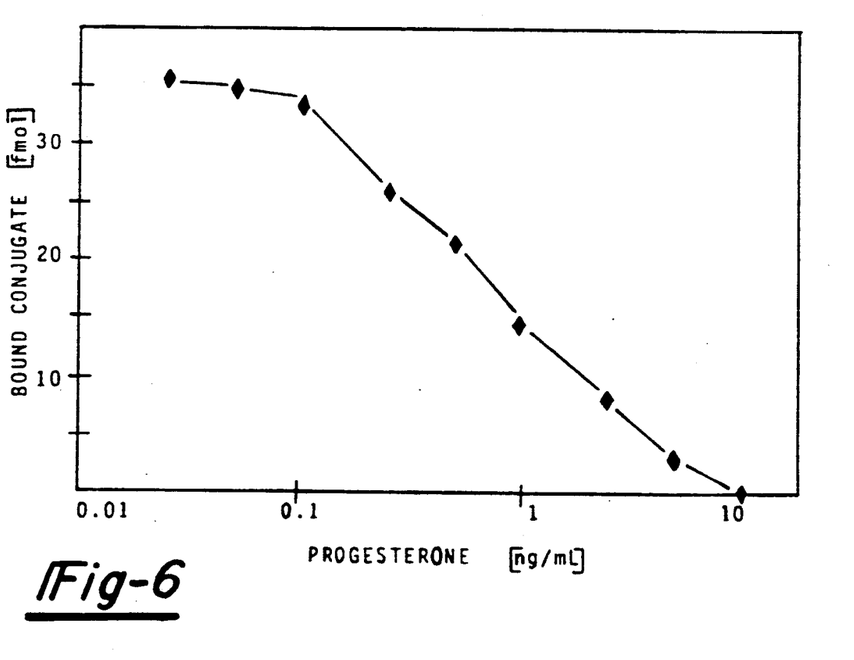
FIG. 6 is a chart showing the signals of the dose response curves from FIG. 10 added and the lowest value set to zero to obtain an additive standard curve.

FIG. 5 shows the dose-response curve for the correlation between progesterone added (abscissa) vs. the amount of heterobifunctional conjugate bound to the solid-phase with the progesterone antibody (full circles) and the HRP antibody (open circles). The additive signals (i.e. subtracting the signal for the HRP-antibody matrix form the signal of the progesterone-antibody matrix at a given progesterone concentration and setting the lowest value to zero) are shown in FIG. 6.

Figure 7:
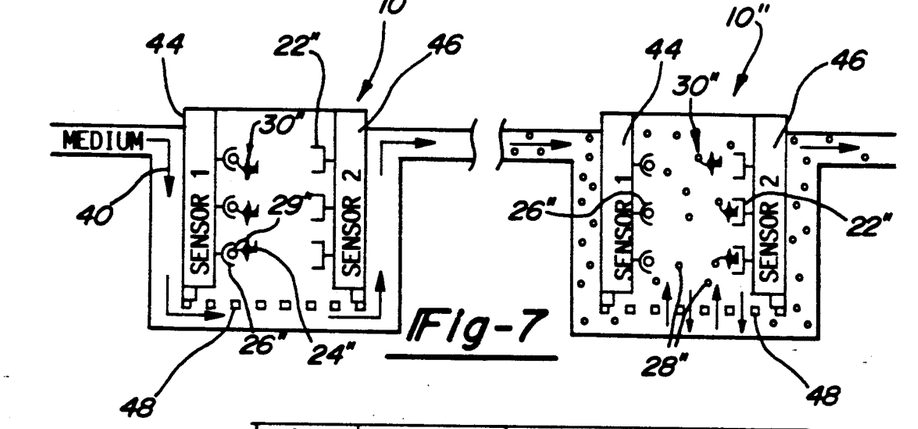
FIG. 7 is a schematic representation of a third embodiment of the present invention and its operation showing continuous monitoring of analytes in a medium stream.

The present invention can utilize two antibodies with a heterobifunctional conjugate and be operated in a reversible mode. Thusly, the present invention is suitable for continuous monitoring of analytes. For this purpose, the internal compartment of the sensor 10" is separated from the medium stream 40 by a semipermeable membrane 48, as shown in FIG. 7. The membrane 48 allows free passage of small molecules but retains the heterobifunctional conjugate 30" within the compartment.

Similar to the previously described embodiments, if a medium stream 40 free of analyte 28" passes by the sensor compartment, the majority of the heterobifunctional conjugate 30" is bound at the sensor 44, as shown in the left of FIG. 7. If the medium contains analyte 28", the equilibrium is shifted towards the binding of a larger portion of the conjugate 30" at the sensor 46 as shown in the right portion of the FIG. 7. Sensors 44 and 46 can be electrodes, such as Clark electrodes. As analyte 28" continually displaces conjugate 30" bound to the antibodies 26" and conjugate 30" then binds to antibody 22", the measured signal from the sensors 44,46 continuously changes as the concentrations of analyte 28" in the medium changes. That is, the amount of analyte 28" is maintained at an equilibrium within and without the membrane 48 to sense continuous changes in the amount of analyte 28" in the medium 40. The medium is continuously flushing analyte into and out of the sensor 10". Thusly, as the amount of analyte 28" in the medium 40 changes, the amount of analyte in the chamber sensor 10" changes. This then affects the equilibrium of conjugate 30" bound either to the antibody 26" or antibody 22". This then modifies the signal generated at the two sensors 44 and 46 thereby allowing for continuous monitoring.

Using the two antibodies 22" and 26" for continuous monitoring has at least three advantages: 1) responses can be obtained on two sensors for each measurement thus increasing the signal yield, 2) the concentration of free or unbound analyte-enzyme conjugate is low at all times, thus reducing the background signal and 3) a higher sensitivity can be obtained because the dissociated conjugate is removed from the bulk solution, favoring binding of the analyte according to the law of mass action.

Applicant has modeled the response of the enzyme-shuttle sensor operated in the reversible mode. Applicant has calculated the optimal concentrations of the two antibodies, the analyte-enzyme conjugate, and the permeability coefficient of progesterone across the semipermeable membrane, utilizing progesterone again as the analyte 28". In addition, applicant has estimated the diffusion coefficient for analyte and conjugate in the internal space of the sensor.

Figure 8:
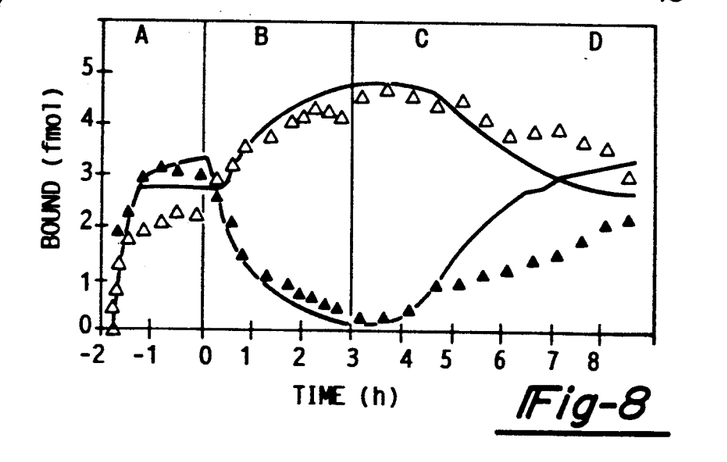
FIG. 8 is a chart showing theoretically determined dose response curves as lines and experimentally measured results as triangles in an enzyme shuttle sensor during exposure of progesterone (20 ng/mL in the external medium)
Figure 9:
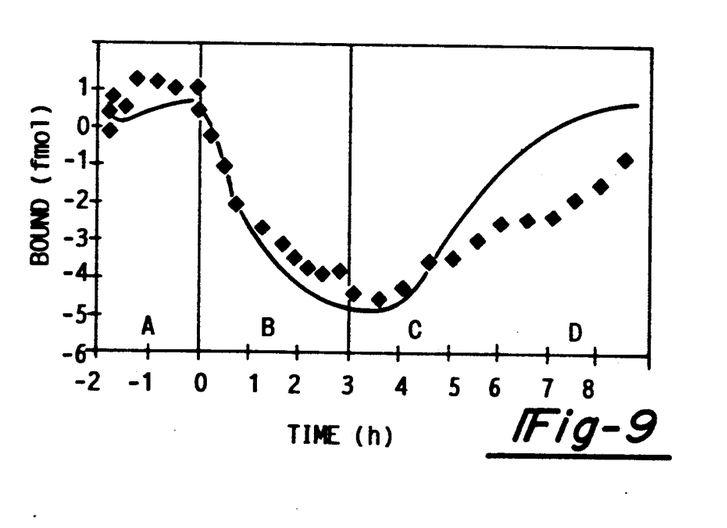
FIG. 9 is a chart showing differential signal from the experiment shown in FIG. 8, the solid line representing the theoretically determined binding curve while the diamond showing the experimentally obtained results.

Applicant has mathematically modeled the response of the sensor and subsequently investigated the predicted performance with experimentally obtained results, as shown in FIGS. 8 and 9. For the model, applicant assumed raising the concentration of progesterone in the external medium from 0 to 20 ng/ml (hour 0), maintaining this concentration for a period of three hours and subsequently exposing the sensor to a medium without progesterone. When newly assembled, the sensor comes to equilibrium within less than two hours. That is, progesterone-enzyme conjugate is bound to sensor 44 and sensor 46 in a certain ratio within the internal compartment. Raising the external progesterone concentration causes an increase of the conjugate on sensor 46 and a decrease on sensor 44. After withdrawal of progesterone, the concentration of conjugate on both sensors remains about the same for an additional hour and then begins to return to the initial state which is reached under these conditions after eight hours which is about five hours after progesterone withdrawal.

Applicant has experimentally investigated the theoretical model under the same conditions as mentioned above. The antibodies to progesterone and horseradish peroxidase were immobilized on discs of polypropylene mesh that fit into sample wells of a microdialyzer (manufactured by Pierce of Rockford, Ill.). The bottoms of the wells were sealed with a semipermeable cellulose membrane (thickness of 8 micrometers, as manufactured by Enka of West Germany). The wells were exposed to a medium stream. Discs were removed at various time intervals and bound progesterone-horseradish oxidase conjugate on the disc was quantitatively measured by color development with tetramethylene benzidine as set forth by Bos et al. Immunoassay, 2 187-204 (1981).

The results of these experiments are shown on FIGS. 8 and 9. Applicant found that the dose-response curves at the two compartments of the sensor follow the theoretically determined response fairly closely during the phase of increased analyte concentration in the external medium (B in FIGS. 8 and 9). There is also close correlation with the predicted model for about 90 minutes after the withdrawal of the analyte (Phase C in FIGS. 8 and 9). Thereafter, the concentration of the analyte-enzyme conjugate deviates from the predicted response. As a result, the initial state (Phase D) is reached at a later time. Applicant attributes the delayed recovery to a slower than expected diffusion of analyte-enzyme molecules from the propylene mesh containing the antienzyme antibody and, possibly to reassociation of the conjugate.

These experiments show the ability of the present invention to be used as a continuous monitoring detector of analytes, such as progesterone, as well as insulin and other small molecules which could pass through a selectively permeable membrane.

What is claimed is:

1. A device for detecting the presence of molecular analytes in a fluid said device comprising:
    an inlet to allow said fluid into the device;
    an outlet to allow said fluid out of the device; and
    a chamber between said inlet and outlet comprising a pair of spaced apart electrodes; first binding means immobilized on one of said electrodes having a predetermined first effective affinity for specifically reversibly binding the analyte; a molecular conjugate of the analyte with a signal generating molecule that generates a detectable signal, said molecular conjugate being reversibly bound to said first binding means; second binding means immobilized on a second of said electrode having a predetermined second effective affinity for reversibly binding said signal generating molecule, said chamber having an opening between said electrodes with a semipermeable membrane disposed over said opening allowing the fluid containing analyte to continuously pass into and out of said chamber through said membrane while said membrane retains said molecular conjugate within said chamber, said chamber continuously receiving, containing and releasing a flow of fluid through said chamber thereby continuously exposing said first and second binding means to the fluid allowing continuously and reversible binding of the analyte in the fluid by competitive displacement of said molecular conjugate and conducting said displaced conjugate to said second binding means where it is bound, said signal generating molecular generating a continuous detectable signal distinguishing binding thereof at said first or second binding means for at least 24 hours thereby continuously indicating the change of analyte concentration in the continuous flow of the fluid; and said signal generating molecule consisting of an enzyme capable of catalyzing a conversion of an enzyme substrate in the fluid into a molecule which can be measured electrochemically by said electrodes.

2. A device as set forth in claim 1 wherein said signal generating means is glucose oxidase and said first binding means is a monoclonal antibody to progesterone and said second binding means is a monoclonal antibody to glucose oxidase.

* * * * *